United States Patent [19]

Möckli

[11] Patent Number: 5,733,343
[45] Date of Patent: Mar. 31, 1998

[54] PROCESS FOR DYEING KERATIN-CONTAINING FIBRES WITH CATIONIC DYES

[75] Inventor: Peter Möckli, Sandgrubenstrasse, Switzerland

[73] Assignee: Ciba Specialty Chemicals Corporation, Tarrytown, N.Y.

[21] Appl. No.: 756,448

[22] Filed: Nov. 26, 1996

Related U.S. Application Data

[63] Continuation of Ser. No. 392,783, filed as PCT/EP94/02077, Jun. 27, 1994, abandoned.

[30] Foreign Application Priority Data

Jul. 5, 1993 [CH] Switzerland ............ 2020/93

[51] Int. Cl.⁶ ............................................. A61K 7/13
[52] U.S. Cl. .................. 8/426; 8/568; 8/573; 8/639; 8/655; 8/657; 8/659; 8/692
[58] Field of Search .................. 8/404, 405, 428, 8/565, 568, 570, 571, 572, 573, 670, 690, 691, 692, 916, 917, 639, 655, 657, 659

[56] References Cited

U.S. PATENT DOCUMENTS

| | | | |
|---|---|---|---|
| 2,708,671 | 5/1955 | Forone et al. | 8/691 |
| 3,221,005 | 11/1965 | Moore et al. | 8/691 |
| 3,336,286 | 8/1967 | Sartori | 8/691 |
| 3,660,008 | 5/1972 | Kissa | 8/589 |
| 3,765,835 | 10/1973 | Clarke et al. | 8/589 |
| 3,787,178 | 1/1974 | Renfrew | 8/691 |
| 3,824,074 | 7/1974 | Bugaut et al. | 8/10 |
| 3,856,788 | 12/1974 | Corbett et al. | 260/244 R |
| 3,869,454 | 3/1975 | Lang et al. | 8/405 |
| 3,985,499 | 10/1976 | Lang et al. | 8/10.1 |
| 4,181,499 | 1/1980 | Koller et al. | 8/568 |
| 4,349,348 | 9/1982 | Tappe et al. | 8/691 |
| 4,705,525 | 11/1987 | Abel et al. | 8/555 |
| 4,705,526 | 11/1987 | Abel et al. | 8/555 |

FOREIGN PATENT DOCUMENTS

| | | |
|---|---|---|
| 2856225 | 7/1979 | Germany. |
| 3287520 | 12/1991 | Japan. |
| 1373081 | 11/1974 | United Kingdom. |

OTHER PUBLICATIONS

Chem. Abstracts, 112 : 145333b, Abstract of DE 3,829,870 Apr. 13, 1989.
Chem. Abstracts, 93 : 53774g, Abstract of JP 80/22,638, Feb. 18, 1980.

*Primary Examiner*—Paul Lieberman
*Assistant Examiner*—Caroline L. Dusheck
*Attorney, Agent, or Firm*—Kevin T. Mansfield

[57] ABSTRACT

Keratin-containing fibres, in particular human hair, are dyed using dyes of formulae (1) to (6) indicated in claim 1. These dyes make it possible to dye by the trichromatic principle even in dark shades.

22 Claims, No Drawings

PROCESS FOR DYEING KERATIN-CONTAINING FIBRES WITH CATIONIC DYES

This is a continuation of application Ser. No. 08/392,783, granted 35 USC 371 filing date of Feb. 28, 1995, now abandoned, originally International application PCT/EP 94/02077 filed Jun. 27, 1994.

The present invention relates to a process for dyeing keratin-containing fibres, in particular human hair, with cationic dyes.

By far the largest proportion of all hair dyeings are carried out, even today, using so-called "oxidation colours", which involves applying small, colourless precursor molecules to the hair and reacting them by an oxidation process to form larger, coloured molecules. Although this produces the most durable ("permanent") colourings, increasing reservations are being voiced about possible toxicological risks posed not only by the substances used as starting materials but also by the oxidation intermediate and end products, whose precise composition is virtually uncontrollable. Further disadvantages are the relatively complicated use and in particular also the hair damage due to the aggressive chemicals used.

The other, so-called "semipermanent" and "temporary" colourings involve the use of ready-prepared dyes, primarily uncharged disperse dyes and relatively sparingly water-soluble acid dyes. Cationic dyes, by contrast, play only a very minor part. As the terms "semipermanent" and "temporary" indicate, these colourings only have a medium to poor fastness level. Especially the cationic dyes have a reputation for poor hydrolysis and light resistance and for uneven colouring of the hair, for example between root and tip (see: John F. Corbett: The Chemistry of Hair-care Products, JSDC August 1976, p. 290). In addition, the known cationic dyes have an insufficient build-up; i.e., even if increased amounts are used, it is impossible to exceed a certain, relatively low, colour strength. For instance, it is not possible to achieve a deep black coloration with the most important cationic hair dyes Basic Yellow 57, Basic Red 76, Basic Blue 99, Basic Brown 16 and Basic Brown 17 which are used in practice. For the same reason it is difficult to tint relatively dark natural hair with these dyes.

It has now been found that surprisingly cationic dyes of the below-indicated formulae have none of these disadvantages. They can be used to achieve in a very simple way and under gentle conditions very deep dyeings having excellent light, shampooing and crock fastness properties. Owing to their extremely clean shades, they also extend the range of possible mixed shades considerably, especially in the direction of the increasingly important brilliant fashion colours.

The present invention accordingly provides a process for dyeing keratin-containing fibres, which comprises treating the fibres with a dye of the formula

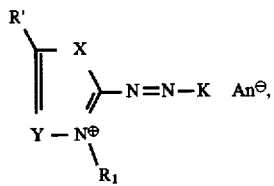

(1)

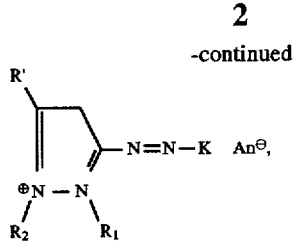

(2)

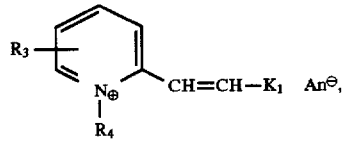

(3)

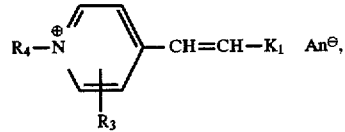

(4)

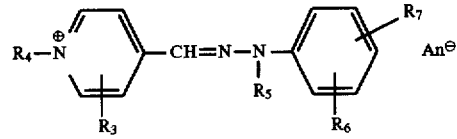

(5)

or

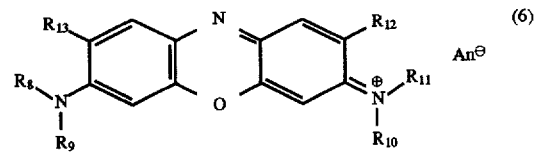

(6)

where
X is —O—, —S— or

Y is —CH=,

—N=,

R is hydrogen, $C_1$–$C_4$alkyl, Cl or nitro,
R' is hydrogen, $C_1$–$C_4$alkyl, Cl, nitro, amino, $C_1$–$C_4$monoalkylamino or di-$C_1$–$C_4$alkylamino,
$R_1$ and $R_2$ are each independently of the other unsubstituted or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl,
$R_3$ is hydrogen, $C_1$–$C_4$alkyl or CN,
$R_4$ is unsubstituted or OH— or CN-substituted $C_1$–$C_4$alkyl,
$R_5$ is hydrogen or $C_1$–$C_4$alkyl,
$R_6$ and $R_7$ are each independently of the other hydrogen, $C_1$–$C_4$alkyl or $C_1$–$C_4$alkoxy, or
$R_5$ and $R_6$ are together with the nitrogen and carbon atoms joining them together a 5- or 6-membered ring,
$R_8$, $R_9$, $R_{10}$ and $R_{11}$ are each independently of the others hydrogen or $C_1$–$C_4$alkyl, with the proviso that at least one of these 4 substituents is $C_1$–$C_4$alkyl and that not all four substituents are ethyl,
$R_{12}$ and $R_{13}$ are each independently of the other hydrogen, $C_1$–$C_4$alkyl or $C_1$–$C_4$alkoxy,
K is the radical of a coupling component of the aniline or phenol series or the radical of a heterocyclic coupling component, $K_1$ is the radical of an aromatic or heterocyclic amine, and $An^{\ominus}$ is a colourless anion, with the proviso that, in the dyes of the formula (1), K is not a radical of N,N-dimethylaniline when X is

Y is —N= and R and $R_1$ are each methyl.

For the purposes of the present invention, alkyl radicals are generally straight-chain or branched $C_1$–$C_4$alkyl groups. Suitable are for example methyl, ethyl, n-propyl, isopropyl, n-butyl, sec-butyl or tert-butyl.

Suitable alkoxy radicals are those having 1 to 4 carbon atoms, e.g. methoxy, ethoxy, propoxy, isopropoxy, n-butoxy, isobutoxy or tert-butoxy.

Halogen is to be understood as meaning fluorine, bromine, iodine or in particular chlorine.

If $R_5$ and $R_6$ are combined with the nitrogen atom and two carbon atoms joining them together into a 5- or 6-membered ring, this ring may contain a further heteroatom, for example oxygen or sulfur. Moreover, the ring may be substituted, for example by hydroxyl, alkoxy, alkyl, halogen, CN or phenyl, or carry a further fused-on benzene ring. Preferred rings formed by $R_5$, $R_6$, the linked carbon atoms and the nitrogen atom are pyrroline, dihydrooxazine and di- or tetrahydropyridine rings carrying 0 to 4 methyl groups.

Suitable anions $An^{\ominus}$ include organic as well as inorganic anions, for example chloride, bromide, sulfate, hydrogensulfate, methosulfate, phosphate, borotetrafluoride, carbonate, bicarbonate, oxalate, formate, acetate, propionate, lactate or complex anions, such as the anion of zinc chloride double salts.

The anion is generally given by the method of preparation. Preferred anions are chloride, sulfate, hydrogensulfate, methosulfate, phosphate, formate, acetate or lactate.

To dye by the process of the invention it is preferable to use a dye of the formula (1) where R' is hydrogen, $C_1$–$C_2$alkyl, amino, $C_1$–$C_2$monoalkylamino or di-$C_1$–$C_2$alkylamino or a dye of the formula (1) where $R_1$ is unsubstituted $C_1$–$C_4$alkyl.

It is likewise preferable to use dyes of the formula (2) where R is hydrogen or $C_1$–$C_4$alkyl or a dye of the formula (2) where $R_1$ is unsubstituted $C_1$–$C_4$alkyl.

Of the dyes of the formula (1), preference is given to those where X is

and especially those where X is

and Y is —CH=.

In the dyes of the formula (1), K is in particular the radical of a coupling component of the formula

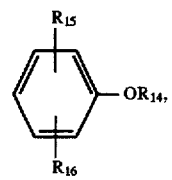

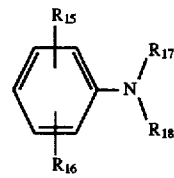

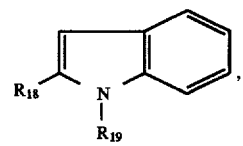

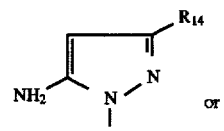

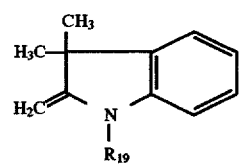

where
$R_{14}$ is hydrogen or unsubstituted or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, $R_{15}$ and $R_{16}$ are each independently of the other hydrogen, $C_1$–$C_4$alkyl, $C_1$–$C_4$alkoxy or halogen, $R_{17}$ and $R_{18}$ are each independently of the other hydrogen, unsubstituted or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, or $R_{17}$ and $R_{18}$ are together with the nitrogen atom joining them together a 5- or 6-membered ring, or $R_{15}$ and $R_{17}$ are together with the nitrogen and carbon atoms joining them together a 5- or 6-membered ring, or $R_{16}$ and $R_{18}$ are together with the nitrogen and carbon atoms joining them together a 5- or 6-membered ring, and $R_{19}$ is hydrogen or unsubstituted or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl.

If $R_{17}$ and $R_{18}$ are to combine with the nitrogen atom joining them together into a 5- or 6-membered ring, this ring is in particular a pyrrolidine, piperidine, morpholine or piperazine ring. These rings can be further substituted, for example by $C_1$–$C_4$alkyl or $C_1$–$C_4$alkoxy. Preference, however, is given to the unsubstituted rings.

If $R_{15}$ and $R_{17}$ or $R_{16}$ and $R_{18}$ are combined with the nitrogen atom and the two carbon atoms joining them together into a 5- or 6-membered ring, this ring may contain a further heteroatom, for example oxygen or sulfur. Moreover, the ring may be substituted, for example by hydroxyl, alkoxy, alkyl, halogen or CN, or carry a further fused-on benzene ring. Preferred rings formed by $R_{15}$ and $R_{17}$ or $R_{16}$ and $R_{18}$ and the carbon atoms joining them together and the nitrogen atom are pyrroline, dihydrooxazine and di- or tetrahydropyridine rings carrying 0 to 4 methyl groups.

In particular K is the radical of a coupling component of the formula

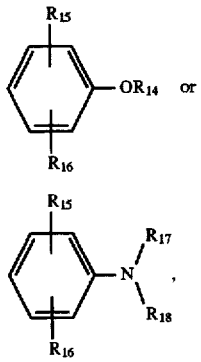

where $R_{14}$ is hydrogen or unsubstituted $C_1$-$C_4$alkyl, $R_{15}$ and $R_{16}$ are each independently of the other hydrogen, $C_1$-$C_4$alkyl, $C_1$-$C_4$alkoxy or halogen, $R_{17}$ and $R_{18}$ are each independently of the other hydrogen or unsubstituted $C_1$-$C_4$alkyl, or $R_{17}$ and $R_{18}$ are together with the nitrogen atom joining them together a pyrrolidine, piperidine, morpholine or piperazine ring, or $R_{15}$ and $R_{17}$ are together with the nitrogen and carbon atom joining them together a pyrrolidine, piperidine, morpholine or piperazine ring, or $R_{16}$ and $R_{18}$ are together with the nitrogen and carbon atom joining them together a pyrrolidine, piperidine, morpholine or piperazine ring, and $R_{19}$ is hydrogen or unsubstituted $C_1$-$C_4$alkyl.

Of very particular interest for the process of the invention are dyes of the formula (1) or (2) where K is the radical of a coupling component of the formula (7) or (8) where $R_{14}$ is methyl or ethyl, $R_{15}$ and $R_{16}$ are each independently of the other hydrogen, methyl, ethyl, methoxy, ethoxy or chlorine, $R_{17}$ and $R_{18}$ are each independently of the other hydrogen, methyl or ethyl, and $R_{19}$ is hydrogen, methyl or ethyl.

Preference is also given to using a dye of the formula (3), (4) or (5) where $R_3$ is hydrogen or methyl or a dye of the formula (3), (4) or (5) where $R_4$ is unsubstituted or hydroxyl-substituted $C_1$-$C_4$alkyl, in particular methyl.

In the dyes of the formula (3) and (4), $K_1$ is in particular the radical of an amine of the formula

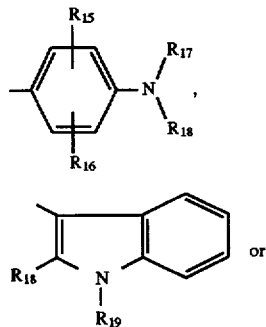

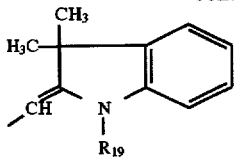

where $R_{15}$ and $R_{16}$ are each independently of the other hydrogen, $C_1$-$C_4$alkyl, $C_1$-$C_4$alkoxy or halogen, $R_{17}$ and $R_{18}$ are each independently of the other hydrogen, unsubstituted or OH—, $C_1$-$C_4$alkoxy-, halogen-, CN—, amino-, $C_1$-$C_4$monoalkylamino- or di-$C_1$-$C_4$alkylamino- substituted $C_1$-$C_4$alkyl, or $R_{17}$ and $R_{18}$ are together with the nitrogen atom joining them together a 5- or 6-membered ring, or $R_{15}$ and $R_{17}$ are together with the nitrogen and carbon atoms joining them together a 5- or 6-membered ring, or $R_{16}$ and $R_{18}$ are together with the nitrogen and carbon atoms joining them together a 5- or 6-membered ring, and $R_{19}$ is hydrogen or unsubstituted or OH—, $C_1$-$C_4$alkoxy-, halogen-, CN—, amino-, $C_1$-$C_4$monoalkylamino- or di-$C_1$-$C_4$alkylamino-substituted $C_1$-$C_4$alkyl, and in particular the radical of an amine of the formula (12), (13) or (14), where $R_{15}$ and $R_{16}$ are each independently of the other hydrogen, methyl, ethyl, methoxy, ethoxy or chlorine, or $R_{15}$ and $R_{17}$ are together with the nitrogen and carbon atoms joining them together a pyrrolidine, piperidine, morpholine or piperazine ring, $R_{17}$ and $R_{18}$ are each independently of the other hydrogen, methyl or ethyl, and $R_{19}$ is hydrogen, methyl or ethyl.

If the process of the invention is carried out using a dye of the formula (5), it is in particular a dye of the formula (5) where $R_5$ is hydrogen or methyl and $R_6$ and $R_7$ are each independently of the other hydrogen, $C_1$-$C_2$alkyl or $C_1$-$C_2$alkoxy, or $R_5$ and $R_6$ are together with the nitrogen and carbon atoms joining them together a pyrrolidine, piperidine, morpholine or piperazine ring.

Of the dyes of the formula (6), preference is given to using those where $R_8$, $R_9$, $R_{10}$ and $R_{11}$ are each independently of the others hydrogen or $C_1$-$C_2$alkyl, with the proviso that at least one of these 4 substituents is $C_1$-$C_2$alkyl and that not all four substituents are ethyl, and $R_{12}$ and $R_{13}$ are each independently of the other hydrogen, $C_1$-$C_2$alkyl or $C_1$-$C_2$alkoxy.

The dyes used according to the invention are known or can be prepared in a manner known per se.

The present invention furthermore provides a process for dyeing keratin-containing fibres, which comprises treating the fibres with a mixture of at least two cationic dyes having a delocalized positive charge and a cation weight below 300, preferably below 280.

Preference is given to using a mixture of at least three cationic dyes with a delocalized positive charge and a cation weight below 280 and in particular a mixture of a yellow, a red and a blue cationic dye with delocalized positive charge and a cation weight below 280.

A very particularly preferred embodiment of the novel process for dyeing keratin-containing fibres comprises treating the fibres with a mixture of at least two cationic dyes of the formula

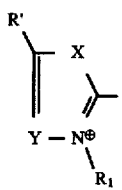 (1)

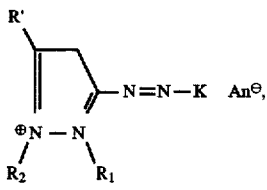 (2)

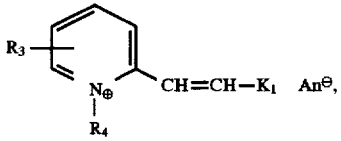 (3)

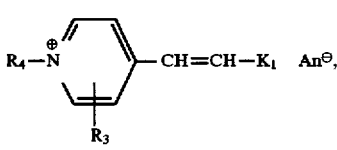 (4)

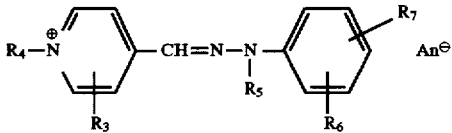 (5)

or

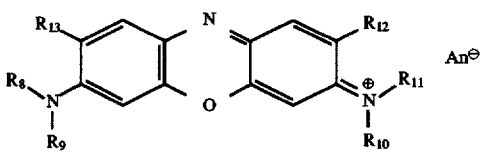 (6)

where
X is —O—, —S—, or

Y is —CH=,

or —N=,
R is hydrogen, $C_1$-$C_4$alkyl, Cl or nitro,
R' is hydrogen, $C_1$-$C_4$alkyl, Cl, nitro, amino, $C_1$-$C_4$monoalkylamino or di-$C_1$-$C_4$alkylamino,
$R_1$ and $R_2$ are each independently of the other unsubstituted or OH—, $C_1$-$C_4$alkoxy-, halogen-, CN—, amino-, $C_1$-$C_4$monoalkylamino- or di-$C_1$-$C_4$alkylamino-substituted $C_1$-$C_4$alkyl,
$R_3$ is hydrogen, $C_1$-$C_4$alkyl or CN,
$R_4$ is unsubstituted or OH— or CN-substituted $C_1$-$C_4$alkyl,
$R_5$ is hydrogen or $C_1$-$C_4$alkyl,
$R_6$ and $R_7$ are each independently of the other hydrogen, $C_1$-$C_4$alkyl or $C_1$-$C_4$alkoxy, or
$R_5$ and $R_6$ are together with the nitrogen and carbon atoms joining them together a 5- or 6-membered ring.

$R_8$, $R_9$, $R_{10}$ and $R_{11}$ are each independently of the others hydrogen or $C_1$-$C_4$alkyl,
$R_{12}$ and $R_{13}$ are each independently of the other hydrogen, $C_1$-$C_4$alkyl or $C_1$-$C_4$alkoxy,
K is the radical of a coupling component of the aniline series or the radical of a heterocyclic coupling component,
$K_1$ is the radical of an aromatic or heterocyclic amine, and $An^\ominus$ is a colourless anion.

The process of the invention is suitable for dyeing furs and also animal and human hair, especially live human hair and domestic animals' hair. As a consequence of the high affinity and the good water solubility of the dyes used, it is possible to do the dyeing at room temperature from aqueous solutions without any assistants whatsoever.

However, it is also possible to use any assistants customary for cationic dyes used in the dyeing of hair, for example wetting agents, swelling agents, penetration aids or scents. In addition, the dyes can be incorporated into shampoos, creams, gels or pastes. Such cosmetic formulations for dyeing hair comprising at least one dye of the above-indicated formulae (1) to (6) and also assistants form a further part of the subject-matter of the present invention.

It has been found that the dyeing effect of the dyes used depends relatively little on the formulation of the dyes.

A particular advantage of the dyes used according to the invention for dyeing hair is that, owing to the good build-up of the dyes, the colourings can be prepared by the trichromatic principle; that is, it is possible by using a yellow, a red and a blue dye in suitable mixtures of these dyes to achieve virtually all shades. In addition, exact prediction of the shades obtained is possible, which is not the case with the so-called "oxidation dyes" owing to the varying composition of the end products.

Using colorimetric methods of measurement it is also possible to obtain on natural, unbleached hair predicted shades having regard to the hair's natural colour by determining its yellow, red and blue content and deducting it from the recipe of the desired shade. This is not feasible with the hair dyes previously used.

The colourings obtained are crock-, water-, wash- and light-fast and stable to permanent-deformation agents, for example thioglycolic acid.

The Examples which follow illustrate the invention. Parts and percentages are by weight. The temperatures are given in degrees Celsius.

EXAMPLE 1

A braid-sewn strand of blond, natural, untreated human hair is dyed at 25° C. for 5 minutes in a conventional manner with a dye emulsion containing 0.1% of the dye of the formula

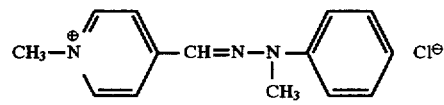

3.5% of Cetearyl Alcohol
1.0% of Ceteareth 80
0.5% of glyceryl mono-di-stearate
3.0% of stearamide DEA
1.0% of stearamphopropylsulfonate
0.5% of polyquaternium-6 and
water to 100%.

Then the hair is thoroughly rinsed with water and air-dried. The result is an intensive brilliant yellow colouring which is many times stronger than a colouring prepared with Basic Yellow 57 in the same way. The light, shampooing and friction fastness properties of the colouring according to the invention are excellent.

EXAMPLE 2

Example 1 is repeated with the dye of the formula

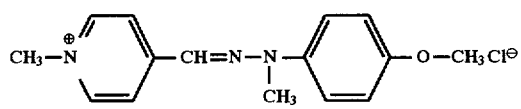

affording an intensively golden yellow colouring with likewise excellent fastness properties.

EXAMPLE 3

A 1% solution of the dye of the formula

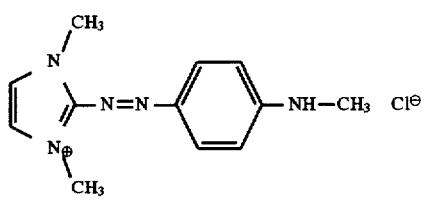

in a surfactant base containing 10% of cocoamphoglycinate and 90% of water is applied to Chinese, bleached yak hair at 25° C. for 5 minutes, and then the hair is thoroughly rinsed and air-dried. The intensively scarlet red colouring obtained is many times stronger than a comparative dyeing with Basic Red 76 and also of distinctly better light fastness.

EXAMPLE 4

A strand of medium brown, untreated human hair is dyed for 5 minutes at room temperature with a dye emulsion containing 0.1% of the dye of the formula

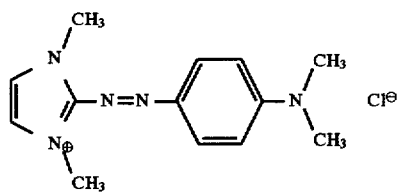

and otherwise having the same composition as the dye emulsion of Example 1. Then the strand of hair is thoroughly rinsed with water and air-dried. The result is a very attractive chestnut-brown shade of the kind which is frequently desired. This shade is impossible to achieve with Basic Red 76 on account of the insufficient build-up of this dye.

EXAMPLE 5

A strand of bleached yak hair is dyed for 5 minutes at 25° C. with a dye emulsion which contains 0.1% of the dye of the formula

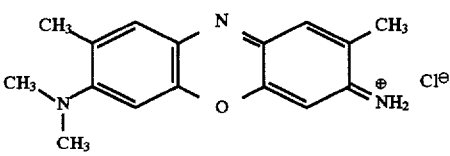

and otherwise has the same composition as the dye emulsion of Example 3. Then the strand of hair is thoroughly rinsed with water and air-dried. The blue colouring obtained is very significantly stronger and more brilliant than a dyeing with Basic Blue 99 prepared in the same way.

EXAMPLE 6

Example 4 is repeated with the red dye replaced by the blue dye of the formula

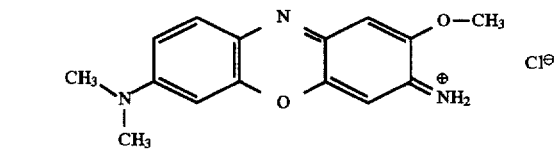

This shifts the original brown of the hair to a mattish brown hue which hides very well undesirable rust-red shades as frequently obtained following oxidation dyeings and lightenings. The scope for these tinting uses is much less with Basic Blue 99.

EXAMPLES 7–70

The method of Examples 1–3 is applied with the dyes listed below in the table, affording colourings on the hair in the specified hues.

| Example | Dye | Hue |
|---|---|---|
| 7 | 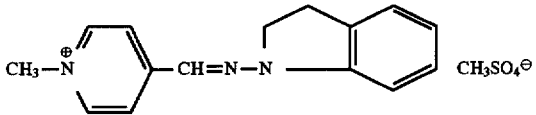 | yellow |
| 8 | 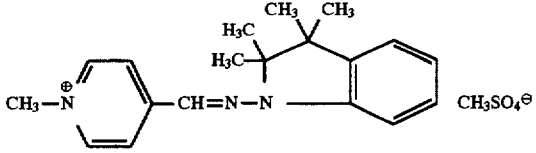 | yellow |

-continued
| Example | Dye | Hue |
|---|---|---|
| 9 | 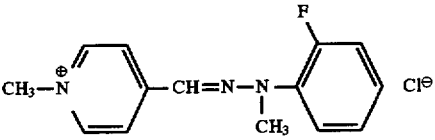 | yellow |
| 10 | 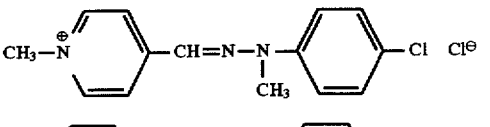 | yellow |
| 11 | 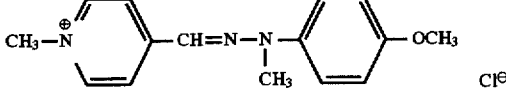 | yellow |
| 12 | 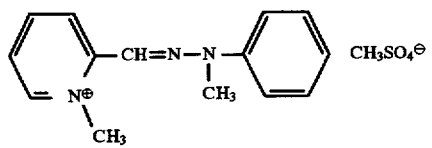 | yellow |
| 13 | 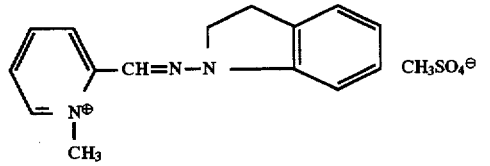 | yellow |
| 14 | 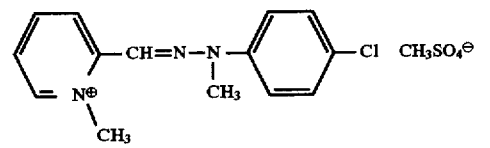 | yellow |
| 15 | 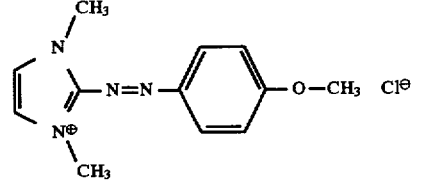 | yellow |
| 16 | 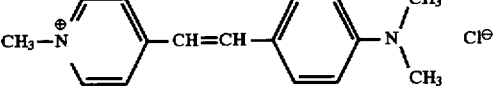 | orange |
| 17 | 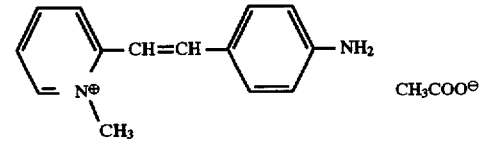 | greenish yellow |
| 18 | 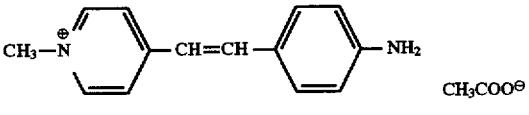 | greenish yellow |
| 19 | 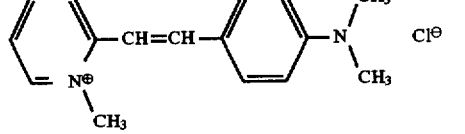 | orange |

-continued

| Example | Dye | Hue |
|---------|-----|-----|
| 20 | [structure: CH₃-N⁺(pyridinium with CH₃)-CH=CH-phenyl-N(CH₃)(C₂H₄CN)] Cl⁻ | yellowish orange |
| 21 | [structure: pyridinium (N⁺-CH₃)-CH=CH-phenyl-N(C₂H₄CN)₂] CH₃SO₄⁻ | yellow |
| 22 | [structure: CH₃-N⁺-pyridinium-CH=CH-indole(NH)] Cl⁻ | greenish yellow |
| 23 | [structure: HO-C₂H₄-N⁺-pyridinium-CH=CH-phenyl(CH₃)-N(CH₃)₂] Cl⁻ | reddish orange |
| 24 | [structure: CH₃-N⁺-pyridinium-CH=CH-CH= indane with gem-dimethyl groups] Cl⁻ | red |
| 25 | [structure: CH₃-N⁺-pyridinium-CH=CH-phenyl fused morpholine with N-CH₃] Cl⁻ | scarlet |
| 26 | [structure: dimethyl triazolium-N=N-indole(N-CH₃)] Cl⁻ | golden yellow |
| 27 | [structure: dimethyl triazolium with CH₃S- substituent -N=N-phenyl-N(CH₃)₂] Cl⁻ | red |
| 28 | [structure: trimethyl pyrazolium-N=N-phenyl fused morpholine with CH₃ groups] Cl⁻ | red |

-continued
| Example | Dye | Hue |
|---|---|---|
| 29 | 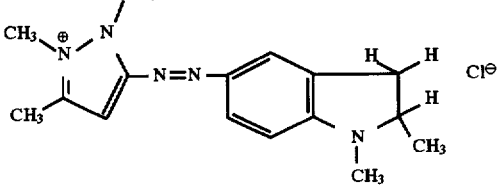 | red |
| 30 | 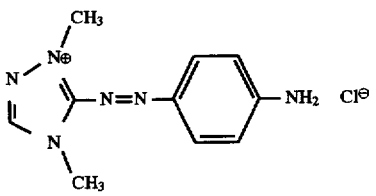 | reddish orange |
| 31 | 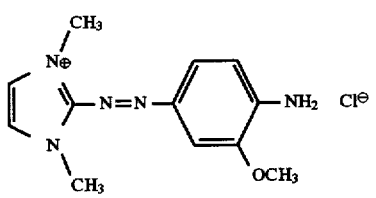 | red |
| 32 | 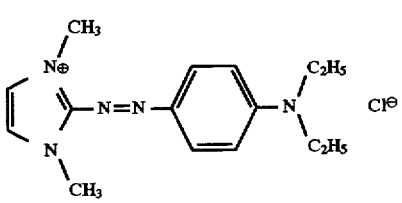 | red |
| 33 | 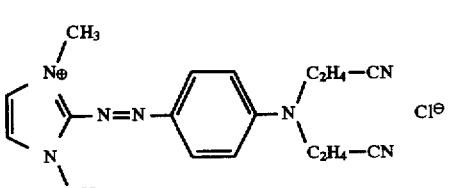 | red |
| 34 | 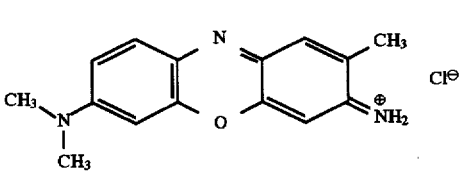 | blue |
| 35 | 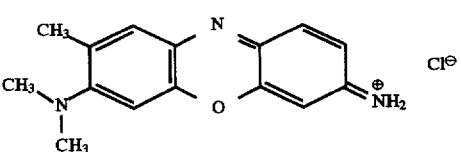 | blue |
| 36 | 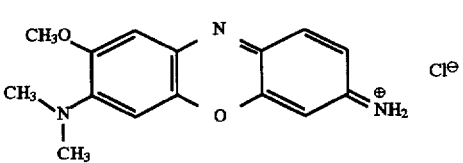 | blue |

-continued

| Example | Dye | Hue |
|---|---|---|
| 37 | (structure) Cl⊖ | blue |
| 38 | (structure) Cl⊖ | blue |
| 39 | (structure) Cl⊖ | blue |
| 40 | (structure) Cl⊖ | blue |
| 41 | (structure) Cl⊖ | blue |
| 42 | (structure) Cl⊖ | blue |
| 43 | (structure) Cl⊖ | blue |
| 44 | (structure) CH₃SO₄⊖ | blue |
| 45 | (structure) Cl⊖ | blue |

-continued

| Example | Dye | Hue |
|---|---|---|
| 46 | (1,3-dimethylimidazolinium)-N=N-C6H4-NH2 Cl⁻ | orange |
| 47 | (1,3-dimethylimidazolinium)-N=N-C6H3(Cl)-NH2 Cl⁻ | orange |
| 48 | (1,3,4,5-tetramethylimidazolinium)-N=N-C6H4-NH2 Cl⁻ | orange |
| 49 | (1,4-dimethyl-1,2,4-triazolium)-N=N-C6H3(OCOCH3)-NH2 Cl⁻ | reddish orange |
| 50 | (1,2-dimethyl-5-methylpyrazolium)-N=N-C6H4-NH(C2H5) Cl⁻ | orange |
| 51 | (1,4-dimethyl-1,2,4-triazolium)-N=N-C6H3(O-CH(CH3)-CH2-N(CH3)-)- Cl⁻ | ruby |
| 52 | (1,3-dimethylimidazolium)-N=N-C6H4-NH(C2H5) Cl⁻ | scarlet |
| 53 | (1,3-dimethylimidazolium)-N=N-C6H4-N(H)-CH2-CH2-NH2 Cl⁻ | scarlet |

-continued

| Example | Dye | Hue |
|---|---|---|
| 54 | (CH₃)(H₃C)N–C(=N⁺(CH₃))–N=N–C₆H₄–NH–CH₂–CH₂–OH  Cl⁻ | scarlet |
| 55 | (CH₃)N–C(=N⁺(CH₃))–N=N–C₆H₄–NH–CH₂–CH₂–CN  Cl⁻ | scarlet |
| 56 | triazolium–N=N–C₆H₃(OCH₃)–N(CH₃)₂  Cl⁻ | scarlet |
| 57 | pyrazolium–N=N–C₆H₄–N(CH₃)₂  Cl⁻ | scarlet |
| 58 | methyl-pyrazolium–N=N–C₆H₄–N(CH₃)₂  Cl⁻ | scarlet |
| 59 | H₂N–C₆H₃–N=C₆H₃(O–)=N⁺H₂  Cl⁻ (phenoxazine) | violet |
| 60 | H₃C,H₂N–C₆H₂–N=C₆H₃(O–)=N⁺H₂  Cl⁻ | violet |
| 61 | thiazolium(N⁺-CH₃)–N=N–C₆H₄–NH₂  Cl⁻ | violet |
| 62 | thiazolium(N⁺-CH₃)–N=N–C₆H₃(Cl)–N(CH₃)₂  CH₃SO₄⁻ | blue |

-continued
| Example | Dye | Hue |
|---|---|---|
| 63 | 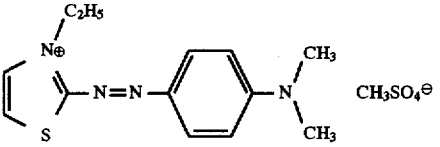 CH₃SO₄⁻ | blue |
| 64 | 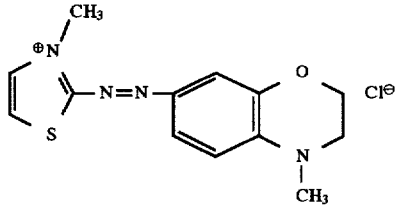 Cl⁻ | blue |
| 65 | 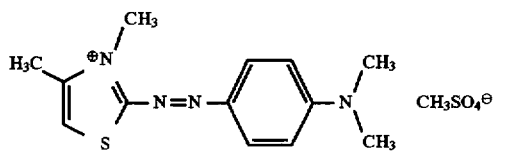 CH₃SO₄⁻ | bluish violet |
| 66 | 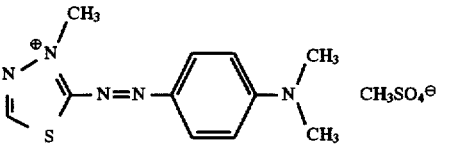 CH₃SO₄⁻ | bluish violet |
| 67 | 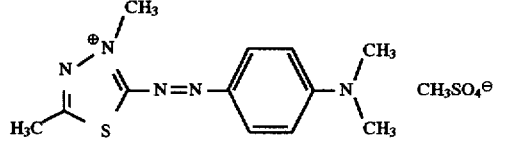 CH₃SO₄⁻ | blue |
| 68 | 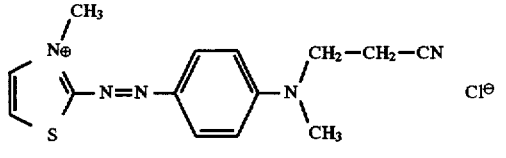 Cl⁻ | violet |
| 69 | 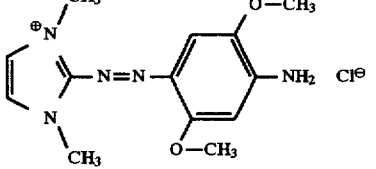 Cl⁻ | violet |
| 70 | 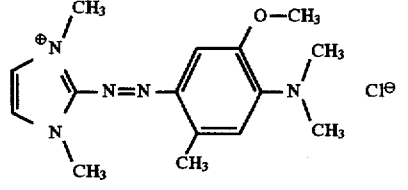 Cl⁻ | violet |
| 71 | 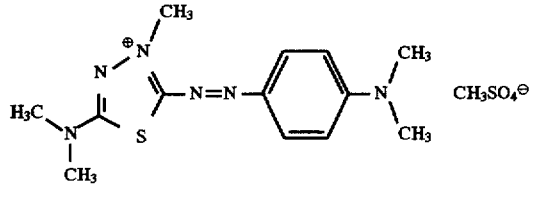 CH₃SO₄⁻ | blue |

| Example | Dye | Hue |
|---|---|---|
| 72 | (structure with CH$_3$SO$_4^\ominus$) | blue |
| 73 | (structure with CH$_3$SO$_4^\ominus$) | blue |
| 74 | (structure with CH$_3$SO$_4^\ominus$) | blue |
| 75 | (structure with CH$_3$SO$_4^\ominus$) | red |

EXAMPLE 76

A braided strand of blond, natural, untreated human hair is treated at 25° C. for 5 minutes with a dye emulsion which has the same composition as the emulsion in Example 1 but contains as dyes 0.11% of the dye of Example 4 and 0.10% of the dye of Example 5. After the strand of hair has been thoroughly rinsed with water and dried, it has a deep violet colour with very good fastness properties.

EXAMPLE 77

Example 76 is repeated with the dyes replaced by 0.08% of the dye of Example 1 and 0.06% of the dye of Example 5, affording a very brilliant green colouring on the hair.

EXAMPLE 78

0.02% of the dye of Example 1 and 0.08% of the dye of Example 5 are dissolved in a surfactant base comprising a 10% aqueous solution of cocoamphoglycinate and this solution is used to dye a strand of bleached yak hair at room temperature for 5 minutes. A bright, brilliant turquoise shade is obtained on the hair.

EXAMPLE 79

Blond, untreated human hair is treated for 20 minutes at room temperature with a dye emulsion which has the same composition as the emulsion in Example 1 but contains as dyes 0.2% of the dye of Example 1, 0.1% of the dye of Example 4 and 0.17% of the dye of Example 6. Thorough rinsing and drying of the hair leaves a deep black colouring having good fastness properties.

EXAMPLE 80

Example 79 is repeated with the dyes replaced by a dye mixture containing 0.138% of the dye of Example 2, 0.082% of the dye of Example 4 and 0.026% of the dye of Example 6, affording a chestnut brown colouring.

EXAMPLE 81

Olive-coloured hair is obtained on repeating Example 79 with the following dye mixture:

0.13% of the dye of Example 2, 0.006% of the dye of Example 4 and 0.032% of the dye of Example 6.

EXAMPLE 82

Example 81 is repeated with a dye mixture containing 0.01% of the dye of Example 2, 0.11% of the dye of Example 4 and 0.21% of the dye of Example 6, affording a dark navy colouring on the hair.

EXAMPLE 83

A surfactant base comprising a 10% aqueous solution of cocoamphoglycinate is used to dissolve 0.036% of the dye of Example 1, 0.034% of the dye of Example 2 and 0.06% of the dye of Example 3 and this solution is used to treat a strand of bleached yak hair for 10 minutes at 25° C. Rinsing and drying leaves a luminously orange dyeing having excellent light, shampooing and friction fastness properties.

What is claimed is:

1. A process for dyeing fibres of human hair, which comprises treating the fibres with a tinctorially effective amount of a dye of the formula

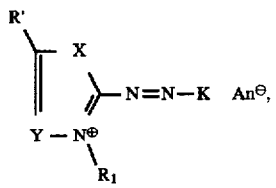 (1)

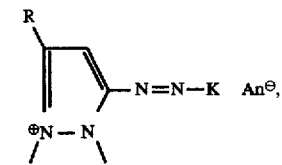 (2)

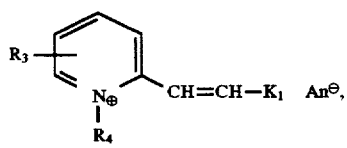 (3)

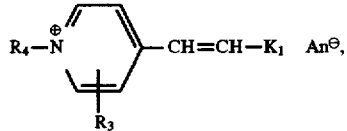 (4)

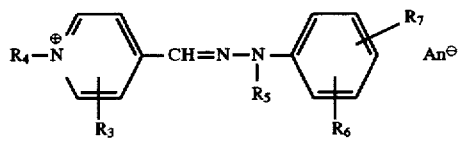 (5)

or

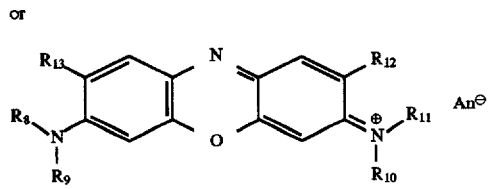 (6)

where

X is

Y is —CH= or

R is hydrogen, $C_1$-$C_4$alkyl, Cl or nitro,

R' is hydrogen, $C_1$-$C_4$alkyl, Cl, nitro, amino, $C_1$-$C_4$monoalkylamino or di-$C_1$-$C_4$alkylamino, $R_1$ and $R_2$ are each independently of the other unsubstituted $C_1$-$C_4$alkyl or OH—, $C_1$-$C_4$alkoxy-, halogen-, CN—, amino-, $C_1$-$C_4$monoalkylamino- or di-$C_1$-$C_4$alkylamino-substituted $C_1$-$C_4$alkyl, $R_3$ is hydrogen, $C_1$-$C_4$alkyl or CN, $R_4$ is unsubstituted $C_1$-$C_4$alkyl or OH—, or CN-substituted $C_1$-$C_4$alkyl, $R_5$ is hydrogen or $C_1$-$C_4$alkyl, $R_6$ and $R_7$ are each independently of the other hydrogen, $C_1$-$C_4$alkyl or $C_1$-$C_4$alkoxy, or $R_5$ and $R_6$ together with the nitrogen and carbon atoms joining them together form a 5- or 6-membered ring, $R_8$, $R_9$, $R_{10}$ and $R_{11}$ are each independently of the others hydrogen or $C_1$-$C_4$alkyl, with the proviso that at least one of these 4 substituents is $C_1$-$C_4$alkyl and that not all four substituents are ethyl, $R_{12}$ and $R_{13}$ are each independently of the other hydrogen, $C_1$-$C_4$alkyl or $C_1$-$C_4$alkoxy, K is the radical of a coupling component of the aniline or phenol series or the radical of a heterocyclic coupling component, $K_1$ is the radical of an amine of the formula

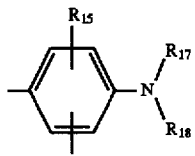 (12)

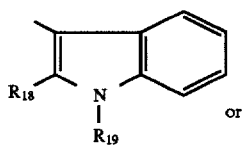 (13)

or

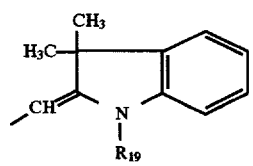 (14)

where $R_{15}$ and $R_{16}$ are each independently of the other hydrogen, $C_1$-$C_4$alkyl, $C_1$-$C_4$alkoxy or halogen, $R_{17}$ and $R_{18}$ are each independently of the other hydrogen, unsubstituted $C_1$-$C_4$alkyl or OH—, $C_1$-$C_4$alkoxy-, halogen-, CN—, amino-, $C_1$-$C_4$monoalkylamino- or di-$C_1$-$C_4$alkylamino-substituted $C_1$-$C_4$alkyl, or $R_{17}$ and $R_{18}$ together with the nitrogen atom joining them together form a 5- or 6-membered ring, or $R_{15}$ and $R_{17}$ together with the nitrogen and carbon atoms joining them together form a 5- or 6-membered ring, or $R_{16}$ and $R_{18}$ together with the nitrogen and carbon atoms joining them together form a 5- or 6-membered ring, and $R_{19}$ is hydrogen or unsubstituted $C_1$-$C_4$alkyl or OH—, $C_1$-$C_4$alkoxy-, halogen-, CN—, amino-, $C_1$-$C_4$monoalkylamino- or di-$C_1$-$C_4$alkylamino-substituted $C_1$-$C_4$alkyl, and An$^\ominus$ is a colourless anion.

2. A process according to claim 1, wherein the dye is of the formula (2) where R is hydrogen or $C_1$-$C_4$alkyl.

3. A process according to claim 1, wherein the dye is of the formula (1) or (2) where $R_1$ is unsubstituted $C_1$-$C_4$alkyl.

4. A process accounting to claim 1, wherein the dye is of the formula (1) where $R_1$ is unsubstituted $C_1$-$C_4$alkyl.

5. A process according to claim 1, wherein the dye is of the formula (1) where Y is —CH=.

6. A process according to claim 1, wherein the dye is of the formula (1) or (2) where K is the radical of a coupling component of the formula

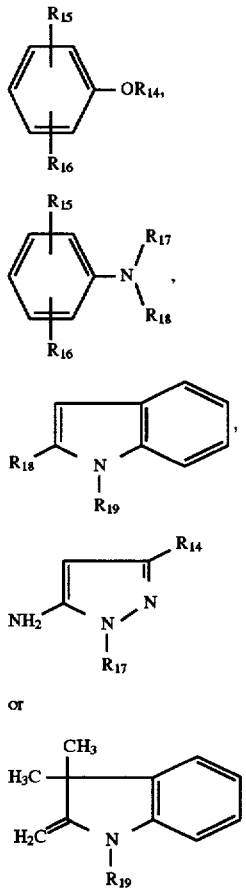

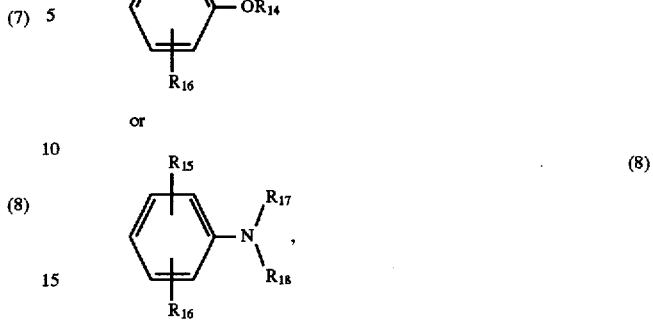

where $R_{14}$ is hydrogen or unsubstituted $C_1$–$C_4$alkyl or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, $R_{15}$ and $R_{16}$ are each independently of the other hydrogen, $C_1$–$C_4$alkyl, $C_1$–$C_4$alkoxy or halogen, $R_{17}$ and $R_{18}$ are each independently of the other hydrogen, unsubstituted $C_1$–$C_4$alkyl or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, or $R_{17}$ and $R_{18}$ together with the nitrogen atom joining them together form a 5- or 6-membered ring, or $R_{15}$ and $R_{17}$ together with the nitrogen and carbon atoms joining them together form a 5- or 6-membered ring, or $R_{16}$ and $R_{18}$ together with the nitrogen and carbon atoms joining them together form a 5- or 6-membered ring, and $R_{19}$ is hydrogen or unsubstituted $C_1$–$C_4$alkyl or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl.

7. A process according to claim 6, wherein the dye is of the formula (1) where K is the radical of a coupling component of the formula where $R_{14}$ is hydrogen or unsubstituted $C_1$–$C_4$alkyl, $R_{15}$ and $R_{16}$ are each independently of the other hydrogen, $C_1$–$C_4$alkyl, $C_1$–$C_4$alkoxy or halogen, $R_{17}$ and $R_{18}$ are each independently of the other hydrogen or unsubstituted $C_1$–$C_4$alkyl, or $R_{17}$ and $R_{18}$ together with the nitrogen atom joining them together form a pyrrolidine, piperidine, morpholine or piperazine ring, or $R_{15}$ and $R_{17}$ together with the nitrogen and carbon atom joining them together form a pyrrolidine, piperidine, morpholine or piperazine ring, or $R_{16}$ and $R_{18}$ together with the nitrogen and carbon atom joining them together form a pyrrolidine, piperidine, morpholine or piperazine ring.

8. A process according to claim 7, wherein the dye is of the formula (1) or (2) where K is the radical of a coupling component of the formula (7) or (8) where $R_{14}$ is methyl or ethyl, $R_{15}$ and $R_{16}$ are each independently of the other hydrogen, methyl, ethyl, methoxy, ethoxy or chlorine, and $R_{17}$ and $R_{18}$ are each independently of the other hydrogen, methyl or ethyl.

9. A process according to claim 1, wherein the dye is of the formula (3), (4) or (5) where $R_3$ is hydrogen or methyl.

10. A process according to claim 1, wherein the dye is of the formula (3), (4) or (5) where $R_4$ is unsubstituted $C_1$–$C_4$alkyl or hydroxyl-substituted $C_1$–$C_4$alkyl.

11. A process according to claim 1, wherein the dye is of the formula (3) or (4) where $K_1$ is the radical of an amine of the formula (12), (13) or (14) where $R_{15}$ and $R_{16}$ are each independently of the other hydrogen, methyl, ethyl, methoxy, ethoxy or chlorine, or $R_{15}$ and $R_{17}$ together with the nitrogen and carbon atoms joining them together form a pyrrolidine, piperidine, morpholine or piperazine ring, $R_{17}$ and $R_{18}$ are each independently of the other hydrogen, methyl or ethyl, and $R_{19}$ is hydrogen, methyl or ethyl.

12. A process according to claim 1, wherein the dye is of the formula (5) where $R_5$ is hydrogen or methyl and $R_6$ and $R_7$ are each independently of the other hydrogen, $C_1$–$C_2$alkyl or $C_1$–$C_2$alkoxy, or $R_5$ and $R_6$ together with the nitrogen and carbon atoms joining them together form a pyrrolidine, piperidine, morpholine or piperazine ring.

13. A process according to claim 1, wherein the dye is of the formula (6) where $R_8$, $R_9$, $R_{10}$ and $R_{11}$ are each independently of the others hydrogen or $C_1$–$C_2$alkyl, with the proviso that at least one of these 4 substituents is $C_1$–$C_2$alkyl and that not all four substituents are ethyl, and $R_{12}$ and $R_{13}$ are each independently of the other hydrogen, $C_1$–$C_2$alkyl or $C_1$–$C_2$alkoxy.

14. A process according to claim 1, wherein the dye is of the formula (1) where R' is hydrogen, $C_1$–$C_2$alkyl, amino, $C_1$–$C_2$monoalkylamino or di-$C_1$–$C_2$alkylamino.

15. A process for dyeing hairs of humans according to claim 1, wherein predeterminable shades are determined with colorimetric methods of measurement.

16. A process for dyeing fibres of human hair, wherein the fibres are treated with a tinctorially effective amount of a mixture of cationic dyes of at least two of the formulae

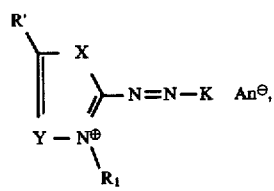 (1)

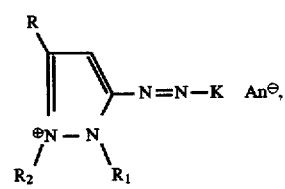 (2)

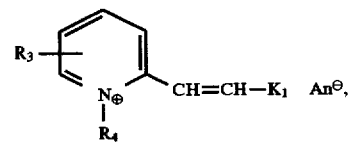 (3)

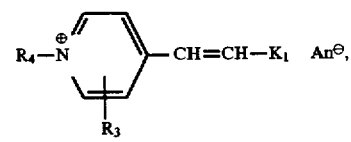 (4)

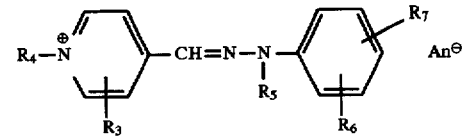 (5)

or

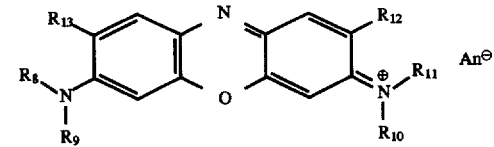 (6)

where

X is

Y is —CH= or

R is hydrogen, $C_1$–$C_4$alkyl, Cl or nitro,

R' is hydrogen, $C_1$–$C_4$alkyl, Cl, nitro, amino, $C_1$–$C_4$monoalkylamino or di-$C_1$–$C_4$alkylamino, $R_1$ and $R_2$ are each independently of the other unsubstituted $C_1$–$C_4$alkyl or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, $R_3$ is hydrogen, $C_1$–$C_4$alkyl or CN, $R_4$ is unsubstituted $C_1$–$C_4$alkyl or OH— or CN-substituted $C_1$–$C_4$alkyl, $R_5$ is hydrogen or $C_1$–$C_4$alkyl, $R_6$ and $R_7$ are each independently of the other hydrogen, $C_1$–$C_4$alkyl or $C_1$–$C_4$alkoxy, or $R_5$ and $R_6$ together with the nitrogen and carbon atoms joining them together form a 5- or 6-membered ring, $R_8$, $R_9$, $R_{10}$ and $R_{11}$ are each independently of the others hydrogen or $C_1$–$C_4$alkyl, $R_{12}$ and $R_{13}$ are each independently of the other hydrogen, $C_1$–$C_4$alkyl or $C_1$–$C_4$alkoxy, K is the radical of a coupling component of the aniline series or the radical of a heterocyclic coupling component, $K_1$ the radical of an amine of the formula

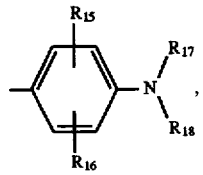 (12)

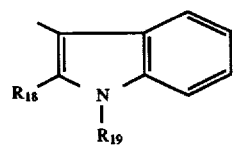 (13)

or

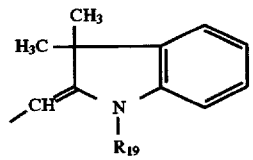 (14)

where $R_{15}$ and $R_{16}$ are each independently of the other hydrogen, $C_1$–$C_4$alkyl, $C_1$–$C_4$alkoxy or halogen, $R_{17}$ and $R_{18}$ are each independently of the other hydrogen, unsubstituted $C_1$–$C_4$alkyl or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, or $R_{17}$ and $R_{18}$ together with the nitrogen atom joining them together form a 5- or 6-membered ring, or $R_{15}$ and $R_{17}$ together with the nitrogen and carbon atoms joining them together form a 5- or 6-membered ring, or $R_{16}$ and $R_{18}$ together with the nitrogen and carbon atoms joining them together form a 5- or 6-membered ring, and $R_{19}$ is hydrogen or unsubstituted $C_1$–$C_4$alkyl or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, and An$^\ominus$ is a colourless anion.

17. A process according to claim 16, wherein the fibres are treated with a mixture of at least two cationic dyes having a delocalized positive charge and a cation molecular weight below 280.

18. A process according to claim 17, wherein the fibres are treated with a mixture of at least three cationic dyes having a delocalized positive charge and a cation molecular weight below 280.

19. A process according to claim 18, wherein the fibres are treated with a mixture of a yellow, a red and a blue cationic dye having a delocalized positive charge and a cation molecular weight below 280.

20. A process for dyeing hairs of humans according to claim 16, which comprises applying to the hairs a mixture of ready-prepared dyes of at least two of the formulae (1) to (6) and wherein predeterminable shades are determined with colorimetric methods of measurement.

21. A process for dyeing hairs of humans according to claim 20, which comprises applying to the hairs a mixture of a yellow, a red and a blue dye, and wherein predeterminable shades are determined with colorimetric methods of measurement.

22. A process for dyeing fibres of human hair, wherein the fibres are treated with a tinctorially effective amount of a mixture of cationic dyes of at least two of the formulae

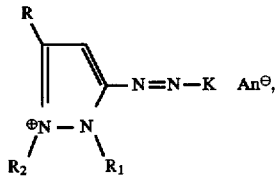
(2)

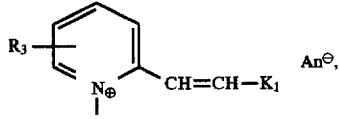
(3)

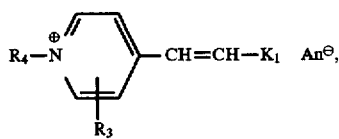
(4)

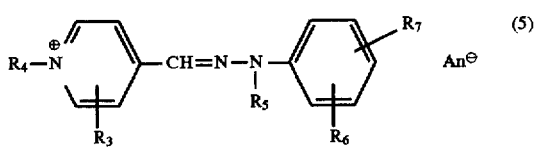
(5)

or

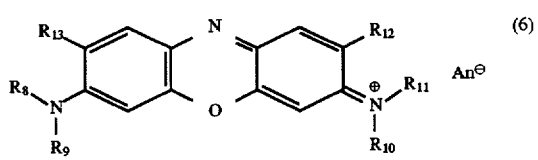
(6)

where

R is hydrogen, $C_1$–$C_4$alkyl, Cl or nitro, $R_1$ and $R_2$ are each independently of the other unsubstituted $C_1$–$C_4$alkyl or OH—, $C_1$–$C_4$alkoxy-, halogen-, CN—, amino-, $C_1$–$C_4$monoalkylamino- or di-$C_1$–$C_4$alkylamino-substituted $C_1$–$C_4$alkyl, $R_3$ is hydrogen, $C_1$–$C_4$alkyl or CN, $R_4$ is unsubstituted $C_1$–$C_4$alkyl or OH— or CN-substituted $C_1$–$C_4$alkyl, $R_5$ is hydrogen or $C_1$–$C_4$alkyl, $R_6$ and $R_7$ are each independently of the other hydrogen, $C_1$–$C_4$alkyl or $C_1$–$C_4$alkoxy, or $R_5$ and $R_6$ together with the nitrogen and carbon atoms joining them together form a 5- or 6-membered ring, $R_8$, $R_9$, $R_{10}$ and $R_{11}$ are each independently of the others hydrogen or $C_1$–$C_4$alkyl, $R_{12}$ and $R_{13}$ are each independently of the other hydrogen, $C_1$–$C_4$alkyl or $C_1$–$C_4$alkoxy, K is the radical of a coupling component of the aniline series or the radical of a heterocyclic coupling component, $K_1$ is the radical of an aromatic or heterocyclic amine, and An$^\ominus$ is a colourless anion.

\* \* \* \* \*